United States Patent [19]
Matsushima et al.

[11] 4,216,309
[45] Aug. 5, 1980

[54] 1-N-ACYL-AMINOGLYCOSIDE-XK-88-5

[75] Inventors: Hideo Matsushima, Machida; Yasuki Mori, Kawasaki, both of Japan

[73] Assignee: Abbott Laboratories, North Chicago, Ill.

[21] Appl. No.: 869,264

[22] Filed: Jan. 13, 1978

[30] Foreign Application Priority Data

Jan. 13, 1977 [JP] Japan .................................. 52/1891

[51] Int. Cl.² ............................................ C07H 15/22
[52] U.S. Cl. .................................. 536/17 R; 424/180; 536/4; 536/18; 536/53
[58] Field of Search .......................................... 536/17

[56] References Cited

U.S. PATENT DOCUMENTS

| | | | |
|---|---|---|---|
| 4,002,608 | 1/1977 | Wright et al. | 536/17 |
| 4,053,591 | 10/1977 | Daniels et al. | 536/17 |

*Primary Examiner*—Johnnie R. Brown
*Attorney, Agent, or Firm*—Fitzpatrick, Cella, Harper & Scinto

[57] ABSTRACT

A new biologically active substance, 1-HABA-seldomycin-5, is produced by chemically modifying the antibiotic XK-88-5. The composition of matter is useful as an antibacterial agent.

2 Claims, 1 Drawing Figure

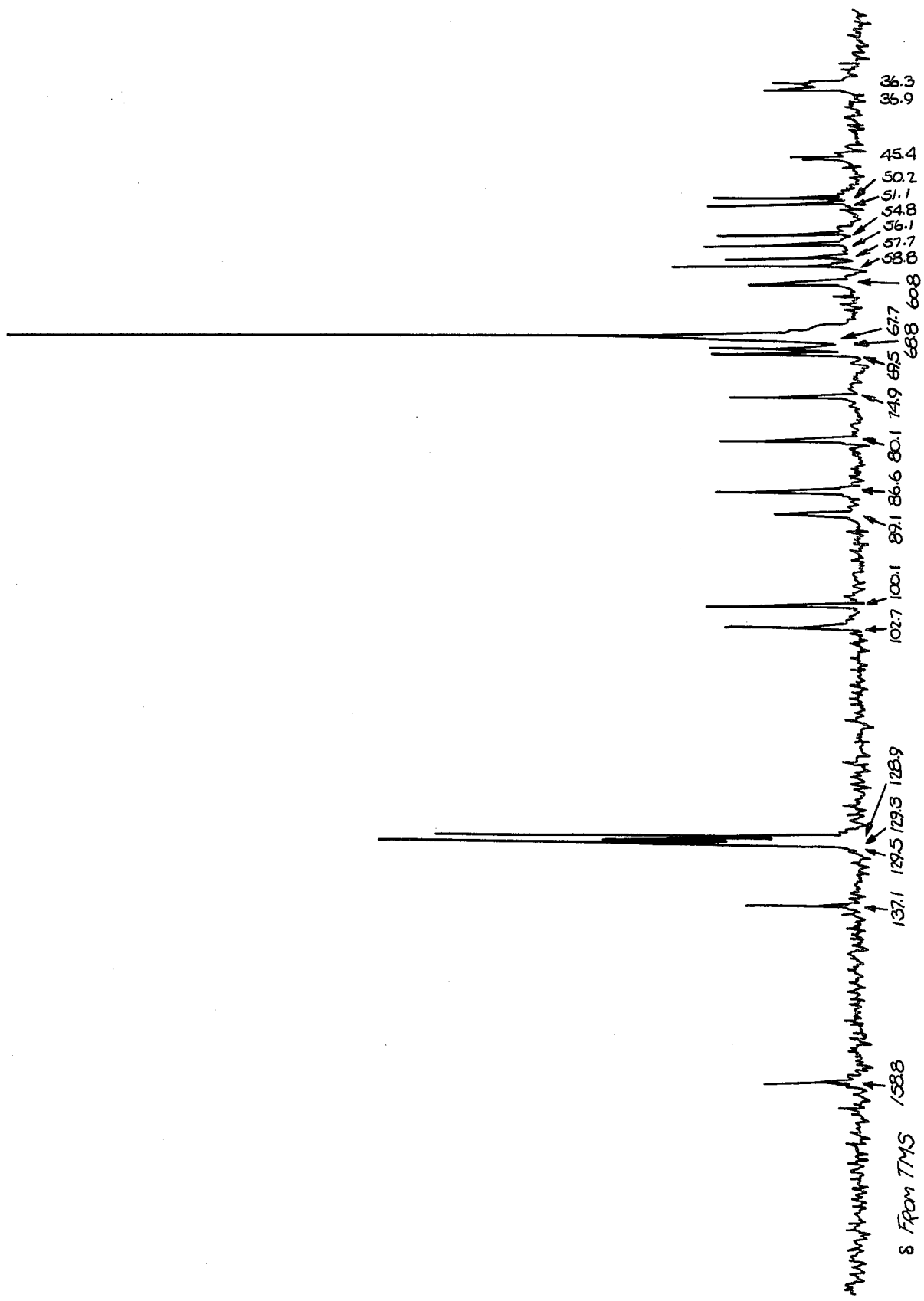

1-N-ACYL-AMINOGLYCOSIDE-XK-88-5

RELATED APPLICATIONS

The present application is directed to a new biologically active substance which is produced by chemically modifying the antibiotic XK-88-5. A process for the production of XK-88 series is disclosed in U.S. Pat. No. 3,939,043 issued on Feb. 17, 1976 and the antibiotic designated XK-88 series are disclosed in U.S. Pat. No. 4,045,610 issued on Aug. 30, 1977. Other patent applications relating to semi-synthetic derivative of XK-88-5 are Ser. No. 815054 filed July 12, 1977, now abandoned and Ser. No. 863,628 and No. 863,629 filed Dec. 23, 1977.

BACKGROUND OF THE INVENTION

The present invention relates to a new biologically active substance and more specifically relates to a new substance comprising an antibiotic, 1-N-(α-hydroxy-γ-amino-butyryl)-XK-88-5, and a process for the production thereof.

Briefly stated, as disclosed in the aforementioned U.S. Pat. No. 3,939,043, the antibiotic XK-88 series are produced by culturing a microorganism such as *Streptomyces hofuensis*, ATCC 21970 under suitable conditions.

XK-88-5 is one factor of the series of an antibiotic XK-88. The XK-88 series of antibiotics are also known as Seldomycins. XK-88-5 (Seldomycin Factor 5) exhibits a high antibacterial activity but it is in demand to produce new derivatives of XK-88-5 useful as antibacterial agents.

It has now been found that a particular derivative of XK-88-5 has excellent antibacterial activities against bacteria having the ability to enzymatically inactive the base compound, XK-88-5.

SUMMARY OF THE INVENTION

The present derivative of XK-88-5 that is, 1-N-(α-hydroxy-γ-aminobutyryl)-XK-88-5 has the following formula [I]:

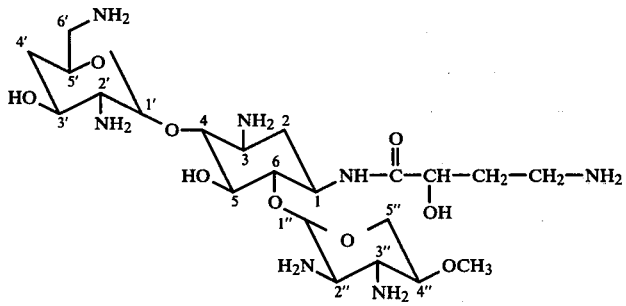

The new compound, 1-N-(α-hydroxy-γ-aminobutyryl)-XK-88-5 exhibits a strong antibacterial activity against various bacteria and particularly has a remarkably strong antibacterial activity against those bacteria that are resistant to kanamycin, lividomycin and gentamicin etc. Accordingly, the antibiotic of the invention is useful as antibacterial agents, and is useful to clean and disinfect laboratory glassware and surgical instruments. Further, the derivative is expected to be effective for the treatment of various infections induced by a variety of Gram-positive and Gram-negative bacteria.

Included in the composition of matter aspect of the invention are the pharmaceutically acceptable non-toxic acid addition salts of the present compound. Suitable acid addition salts are prepared in known manner by, for example, reacting one molecule of 1-N-(α-hydroxy-γ-aminobutyryl)-XK-88-5 with one to six equimole acid.

According to the present invention, the new derivative of XK-88-5 or pharmaceutically acceptable, non-toxic acid addition salts thereof is prepared by introducing an α-hydroxy-γ-aminobutyryl group to the amino group bonded to the carbon atom at the 1-position of XK-88-5.

DETAILED DESCRIPTION OF THE INVENTION

In accordance with the present invention, 1-N-(α-hydroxy-γ-aminobutyryl)-XK-88-5 which is prepared by acylating XK-88-5 or the derivatives thereof whose amino group bonded to the carbon atom at the 6'-position is protected, with an acylating agent or compounds functionally equivalent thereto, to prepare an intermediate compound and thereafter removing the substituted amino-protecting groups in a known manner. If desired, 1-N-(α-hydroxy-γ-aminobutyryl)-XK-88-5 may be thereafter converted to non-toxic acid addition salts by conventional method.

An antibiotic XK-88-5 used as the starting material of the present compound is disclosed and claimed in U.S. Pat. No. 4,045,610 issued on Aug. 30, 1977 and process for the production by fermentation thereof are described and claimed in U.S. Pat. No. 3,939,043 issued on Feb. 17, 1976 which descriptions are incorporated herein by reference.

XK-88-5 is a water-soluble basic antibiotic having a broad antibacterial activity against Gram-positive and Gram-negative bacteria. The antibiotic has the molecular formula of $C_{18}H_{38}N_6O_7$, the molecular weight of 450 and the following structural formula (II):

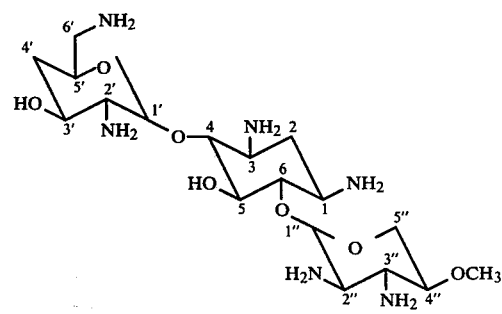

The present compound, 1-N-(α-hydroxy-γ-aminobutyryl)-XK-88-5 which is produced by the two following methods, (A) or (B).

Method (A)

XK-88-5 is reacted with an acylating agent such as α-hydroxy-γ-amino-protected aminobutyric acid represented by the general formula (III):

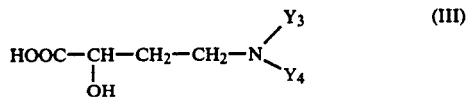

(wherein one of $Y_3$ and $Y_4$ is hydrogen atom and the other one is an amino-protecting group or $Y_3$ and $Y_4$ may form a ring with the nitrogen atom to which $Y_3$ and $Y_4$ are bonded) and reactive derivatives at the carboxyl group which are functionally equivalent thereto to form a compound represented by the general formula (IV):

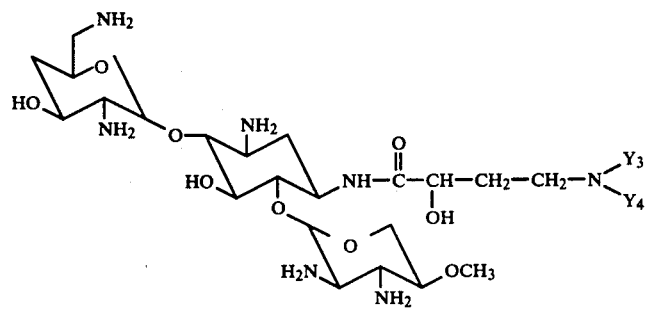

[IV]

(wherein $Y_3$ and $Y_4$ have the same significance as defined above). Thereafter, the amino-protecting groups of the compound represented by the general formula (IV), $Y_3$ and $Y_4$, are eliminated in a known manner to form a compound represented by the formula (I).

The present method is one of known methods described in, for example; M. Bodansky et al: *Peptide Syntheses*, pages 21–41 and 75–135 (1966) (John Wiley & Sons, Inc., U.S.A.) (referred to as "Reference A" hereinafter), A. Kappor: *Journal of Pharmaceutical Sciences*, Vol. 59, pages 1–27 (1970) (referred to as "Reference B" hereinafter) and M. Bodansky et al: *Syntheses*, pages 453–463 (1972) (referred to as "Reference C" hereinafter).

In the acylating reaction, one mole of XK-88-5 dissolved in an appropriate solvent is reacted with 0.1 to 3.0 mols, preferably, 0.5 to 1.3 mols of an acylating agent. The reaction is usually carried out at a temperature from −20° to 100° C., preferably, from 0° to 40° C. for 0.1 to 48 hours.

As the acylating agent for this reaction, α-hydroxy-γ-aminoprotected aminobutyric acid and functional derivatives at the carboxyl groups thereof having an acylating ability may be used.

As the amino-protecting group of α-hydroxy-γ-amino-protected aminobutyric acid, any readily eliminable protecting group usually used in peptide syntheses may be used. Such protecting groups and the corresponding protecting reagents which can introduce the protecting group are described for example in Reference A, Reference B and Reference C mentioned above.

Examples of the preferred protecting groups and the corresponding reagents are shown below.

| protecting group | protecting reagent |
|---|---|
| ![benzyloxycarbonyl] | ![benzyloxycarbonyl-OSu and benzyloxycarbonyl-X] |
| $C(CH_3)_3-O-CO-$ | $[C(CH_3)_3-O-CON_3]$ |
| $CH_3-O-CO-$ | $(CH_3-O-COX)$ |
| $C_2H_5-O-CO-$ | $(C_2H_5-O-COX)$ |
| $X-CH_2-CO-$ | $(X-CH_2-COX, XCH_2-COOH)$ |
| $C(C_6H_5)_3-$ | $[C(C_6H_5)_3-X]$ |

| protecting group | protecting reagent |
| --- | --- |
| ![o-nitrophenylthio group] | ![o-nitrophenylsulphenic acid] |
| ![phthaloyl group] | ![N-ethoxycarbonylphthalimide] |

[R₁ and R₂ in the above formulae may be the same or different and are H, OH, NO₂, Cl, Br, I, alkyl groups having 1 to 5 carbon atoms or alkoxy groups having 1 to 5 carbon atoms, and X is Cl, Br or I]

As the functional derivative at the carboxyl group, various functional derivatives at carboxyl groups usually used in peptide synthesis such as acid halides, acid azide, mixed acid anhydride, and reactive ester, can be used; and the concrete examples are described in, for example, the afore-mentioned Reference A, Reference B and Reference C.

As preferred functional derivatives, those having a structure in which the hydroxy group of the carboxyl group is substituted by one of the following groups are appropriate:

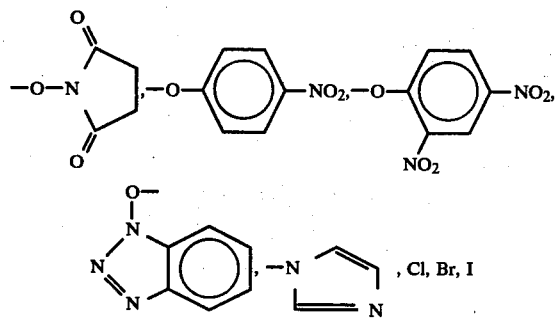

Particularly preferred acylating agents are those having a structure in which the hydroxy group of the carboxyl group is substituted by

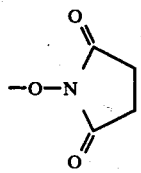

The acylating reaction readily proceeds in the presence of dicyclohexylcarbodiimide. Certain cyanamides, etc. may be used in place of dicyclohexylcarbodiimide.

As the solvent for the acylating reaction, is used at least one solvent selected from the group consisting of water, alcohols such as methanol, ethanol, propanol and butanol, amides such as N,N-dimethylformamide and dimethylacetamide, tetrahydrofuran, dioxane, ethylene glycol, dimethyl ether, pyridine, dimethyl sulfoxide, acetonitrile, acetone, N-lower alkylpiperidine, and so on. A mixed solvent of water and an organic solvent (1:0.1-1:10 by volume) is especially preferred.

Thus, α-hydroxy-γ-amino-protected aminobutyryl group can be introduced to the amino group bonded to the carbon atom at the 1-position of XK-88-5.

The amino-protecting groups of the compound obtained by the acylating reaction mentioned above and represented by the general formula (IV) can be eliminated in a known manner of eliminating amino-protecting groups. The known manner is described for example in Reference A, Reference B, Reference C and K. Undheim et al: *Journal of Chemical Society*, Parkin Transaction I. page 829 (1973). For example, when the amino protecting groups are phthaloyl groups, elimination is accomplished with hydrazine; when the amino protecting groups are carbomethoxy groups or carboethoxy groups, elimination is accomplished with barium hydroxide; when the amino protecting groups are tertiary-butoxy carbonyl groups, elimination is accomplished with formic acid or trifluoroacetic acid; when the amino protecting groups are orthonitrophenylsulphenyl groups, elimination is accomplished with 3-nitropyridine-2-thione.

The desired product is recovered and purified from the thus obtained reaction mixture by a column chromatography using adsorbents such as ion exchange resins, silica gel, alumina and cellulose, or a thin layer chromatography using silica gel, alumina or cellulose.

Method (B)

In this method, the amino group at the 6'-position of XK-88-5 is protected to prepare a compound represented by the formula [V]:

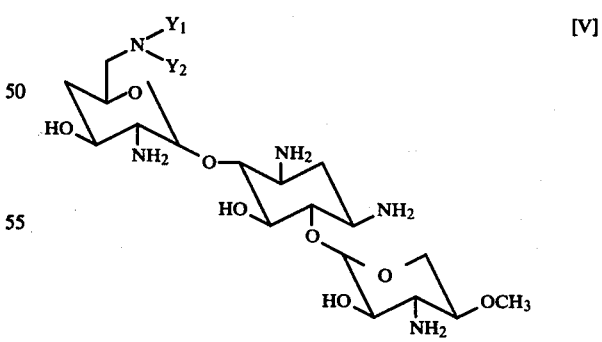

(wherein Y₁ and Y₂ represent hydrogen atom or amino-protecting group or Y₁ and Y₂ may form a ring with the nitrogen atom to which Y₁ and Y₂ are bonded, but Y₁ and Y₂ are not hydrogen atom at the same time) in advance, before the amino group at the 1-position of XK-88-5 is subjected to acylating reaction.

The protection of the amino group at the 6'-position of XK-88-5 is carried out by reacting XK-88-5 with an amino-protecting reagent in an appropriate solvent in a known manner, for example, described in Reference A, Reference B and Reference C.

It is preferable to react one mole of XK-88-5 with 0.1 to 3.0 mols, favourably, 0.3 to 1.5 mols of the protecting reagent at a temperature of from −20° to 50° C., preferably, from −10° to 30° C.

The preferred examples of the protecting reagent and the solvent for this reaction are given and described in connection with the process of acylating XK-88-5 which is previously described.

Process for acylating the compound whose amino group bonded to the carbon atoms at the 6'-position is protected and process for eliminating the amino protecting groups from the resulted acylated product are carried out in a manner as in Method A mentioned above.

Minimum inhibitory concentrations (MIC) (mcg/ml) of the present compound were determined by agar-dilution method at pH 8.0 and the results are shown in Table 1 in comparison with the starting material, XK-88-5.

| Name of microorganism | Strain No. | Resistance | Present compound | XK-88-5 |
|---|---|---|---|---|
| Streptococcus faecalis | KY4280 | | 10 | 5.0 |
| Pseudomonas aeruginosa | KY4276 | | 10 | 5.0 |
| Staphylococcus aureus | KY4279 | | 0.08 | 0.08 |
| Escherichia coli | KY4271 | | 0.32 | 0.16 |
| Escherichia coli | KY8310 | Resistance depend upon other than R-factor | 2.5 | >80 |
| Escherichia coli | KY8302 | Resistant to kanamycin, lividomycin | 2.5 | >80 |
| Escherichia coli | KY8315 | | 2.5 | >80 |
| Escherichia coli | KY8331 | | 0.32 | >80 |
| Escherichia coli | KY8332 | | 1.25 | 0.64 |
| Escherichia coli | KY8321 | Resistant to neomycin, kanamycin and gentamicin | 0.64 | 0.64 |
| Escherichia coli | KY8348 | | 0.64 | 5.0 |
| Bacillus subtilis | KY4273 | | 0.02 | 0.04 |
| Bacillus cereus | KY3308 | | 0.32 | 0.64 |
| Sarcina lutea | KY4122 | | 0.64 | 1.25 |
| Alcaligenes faecalis | KY3101 | | 0.64 | 0.64 |
| Proteus vulgaris | KY4277 | | 1.25 | 0.32 |
| Shigella sonnei | KY4281 | | 1.25 | 0.64 |
| Salmonella typhosa | KY4278 | | 0.64 | 0.16 |
| Klebsiella pneumoniae | KY4275 | | 0.16 | 0.08 |

Non-toxic acid addition salts of the present compound also have as broad an antibacterial spectrum as the free base of the present compound, and similar effects can be expected.

Herein the non-toxic acid addition salts mean mono-, di-, tri-, tetra-, penta- and hexa-salts, which are formed by reaction of one molecule of 1-N-(α-hydroxy-γ-aminobutyryl)-XK-88-5 with 1 to 6 molecules of pharmaceutically acceptable non-toxic acid. Those pharmaceutically acceptable non-toxic acids include inorganic acids such as hydrochloric acid, hydrobromic acid, hydroiodic acid, sulfuric acid, phosphoric acid, carbonic acid, nitric acid, etc., and organic acids such as acetic acid, fumaric acid, maleic acid, malic acid, citric acid, succinic acid, mandelic acid, ascorbic acid, tartaric acid, etc. and amino acids such as aspartic acids, etc.

Practice of the certain specific embodiments of the present invention is illustrated by the following representative examples.

EXAMPLE 1

Preparation of 6'-N-benzyloxycarbonyl-XK-88-5
[Compound of $Y_1$=H and $Y_2$=a benzyloxycarbonyl group in Formula V]

In this example, 1.60 g (3.56 mmol) of an antibiotic XK-88-5 (free base) is dissolved in a mixed solvent of 60 ml of water and 60 ml of ethylene glycol dimethyl ether. Separately, 0.93 g (3.74 mmol) of N-benzyloxycarbonyloxysuccinimide is dissolved in 10 ml of ethylene glycol dimethyl ether and the solution is cooled. The cooled solution is then added dropwise to the solution of XK-88-5 cooled to 2° C. over a period of 20 minutes with stirring. The reaction mixture is allowed to stand for 20 hours in a refrigerator and the precipitate (0.31 g, assumed to be poly-N-benzyloxycarbonyl-XK-88-5) is removed by filtration. The filtrate is concentrated to dryness under reduced pressure maintaining the temperature under 35° C. and the residue is dissolved in 30 ml of water.

The solution is charged into a column packed with 160 ml of Amberlite CG-50 ($NH_4^+$ form) (trademark for a weakly acidic cation exchange resin produced by Rohm & Haas Co., U.S.A.). After washing the resin with 460 ml of water, elution is carried out with 460, 640 and 440 ml respectively of 0.1 N, 0.2 N and 0.3 N aqueous ammonias in turn.

The eluate is taken in 20 ml portions while checking the components in the eluate by thin layer chromatography. Fraction Nos. 28–34 are combined and concentrated to dryness under reduced pressure. The residue (0.95 g) is dissolved in 14 ml of a mixed solvent of n-butanol, ethanol, chloroform, concentrated aqueous ammonia and water (4:5:2:1:2 by volume) and the solution is charged into a column packed with 38 g of silica gel (produced by Merck & Co., Inc., U.S.A.). Elution is carried out with 448 ml and 368 ml of the following two mixed solvents in turn. The former consists of n-butanol, ethanol, chloroform and concentrated aqueous ammonia (4:5:2:1 by volume) and the latter consists of a mixed solvent of the same components as above (4:5:2:2 by volume). The eluate is taken in 8 ml portions while checking the components in the eluate by thin layer chromatography. Fraction Nos. 35–83 are combined and concentrated to dryness under reduced pressure to obtain 0.55 g of basic white powder. This powder has the following physicochemical properties.

(1) Melting point: 113°–116° C.
(2) Specific rotation: $[\alpha]_D^{24}$ = +101° (c=0.505, $H_2O$)
(3) Elementary analysis as $C_{26}H_{44}N_6O_9 \cdot H_2O$:
Calculated (%) C=51.80, H=7.71, N=13.95 Found (%) C=51.97, H=7.47, N=13.33
(4) Thin layer chromatography (hereinafter abridged as TLC) using silica gel plate Rf=0.62 [developer: a mixed solvent of n-butanol, ethanol, chloroform and concentrated aqueous ammonia (4:5:2:5 by volume), coloring agent: ninhydrin]

(5) Infrared absorption spectrum (KBr, cm$^{-1}$) 1690–1710

(6) $^{13}$C-nuclear magnetic resonance spectrum (in D$_2$O) shown in FIG. 1

From the above physicochemical properties, the compound is identified as 6'-N-benzyloxycarbonyl-XK-88-5.

EXAMPLE 2

Preparation of 1-N-[L-(−)-α-hydroxy-γ-aminobutyryl]-XK-88-5

In this example, 0.86 g (1.47 mmol) of 6'-N-benzyloxycarbonyl-XK-88-5 obtained in the same manner as described in Example 1 is dissolved in a mixed solvent of 40 ml of water and 20 ml of ethylene glycol dimethyl ether. Separately, 0.57 g (1.63 mmol) of N-hydroxysuccinimide ester of L-(−)-α-hydroxy-γ-N-benzyloxycarbonylaminobutyric acid [Kawaguchi, et. al, *Journal of Antibiotics* vol. XXV, 695 (1972)] is dissolved in 20 ml of ethylene glycol dimethyl ether. The solution is added dropwise to the solution of 6'-N-benzyloxycarbonyl-XK-88-5 at 23° C. over a period of 35 minutes with stirring and the resultant solution is stirred for 24 hours. Then, the solution is concentrated to dryness under reduced pressure while maintaining the temperature under 35° C. whereby ethylene glycol dimethyl ether and water is distilled off. To the residue 50 ml of methanol and 50 ml of water are added. To the resultant solution is added 0.52 g of 10% palladium-carbon and 1 ml of acetic acid. Reaction is carried out at 23° C. with stirring by passing hydrogen gas through the mixture until white turbidity of barium hydroxide aqueous solution as a trap ceases to occur (for about 5 hours). Then, the mixture is subjected to filtration and palladium-carbon is washed with 230 ml of 1 N aqueous ammonia. The filtrate and washings are separately concentrated to dryness under reduced pressure while maintaining the temperature under 35° C. The residues are combined and dissolved in 20 ml of water and the solution is charged into a column packed with 90 ml of Amberlite CG-50 (NH$_4$$^+$ form). After washing the resin with 300 ml of water, elution is carried out with 330, 345, 450 and 435 ml respectively of 0.1, 0.2, 0.3 and 0.4 N aqueous ammonia in turn. The eluate is taken in 15 ml portions while checking the components of the eluate. The check is carried out both by TLC (color agent: ninhydrin) and by bioassay using *Staphylococcus aureus* ATCC 6538P and *Escherichia coli* KY 8302. Fraction Nos. 84–100 are combined and concentrated to dryness under reduced pressure. The residue (70 mg) is dissolved in 4 ml of a mixed solvent of n-butanol, ethanol, chloroform and concentrated aqueous ammonia (4:5:2:3 by volume) and the solution is charged into a column packed with 4 g of silica gel (produced by Merck & Co., Inc., U.S.A.). Elution is carried out with 57 ml and 44 ml of the following two mixed solvents in turn. The former consists of n-butanol, ethanol, chloroform and concentrated aqueous ammonia (4:5:2:3 by volume) and the latter consists of the same components as above (4:5:2:4 by volume). The eluate is taken in 1 ml portions while checking the components of the eluate. The check is carried out in the same manner as described above. Fraction Nos. 62–75 are combined and concentrated to dryness under reduced pressure to obtain 45 mg of basic white powder. This powder has the following physicochemical properties.

(1) Melting point: 150°–154° C.

(2) Specific rotation: [α]$_D^{20}$ = +81° (c=0.133, H$_2$O)

(3) Elementary analysis as C$_{22}$H$_{45}$N$_7$O$_9$.H$_2$CO$_3$.½H$_2$O: Calculated (%) C=44.35, H=7.78, N=15.75 Found (%) C=45.06, H=7.27, N=15.05

(4) TLC by silica gel (produced by Eastman Kodak Co., U.S.A., sheet No. 13181)

Rf=0.24 [developer: a mixed solvent of n-butanol, ethanol, chloroform and concentrated aqueous ammonia (4:5:2:5 by volume), coloring agent: ninhydrin]

Rf=0.43 [developer: a mixed solvent of methanol, concentrated aqueous ammonia and chloroform (3:2:1 by volume), coloring agent: ninhydrin] Further, in TLC using silica gel plate (produced by Merck & Co., Inc., U.S.A., TLC plate art. 5714) and lower part of a mixed solvent of chloroform, methanol and concentrated aqueous ammonia (1:1:1 by volume) as a developer, 2 spots (large and small) are observed.

large spot: Rf=0.16 small spot: Rf=0.20

The ratio of size with the naked eye is about 10:1.

(5) Infrared absorption spectrum (KBr, cm$^{-1}$) 1635, 1660, 1565

(6) Mass spectrum:

1-N-[L-(−)-α-hydroxy-γ-aminobutyryl]-XK-88-5 is converted to the N-acetyl-O-trimethylsilyl derivative and the mass spectrum of the derivative is measured. Comparatively intensive fragment peaks are observed at m/e of 520, 492, 301 and 229. These fragment peaks seem to denote the following structures.

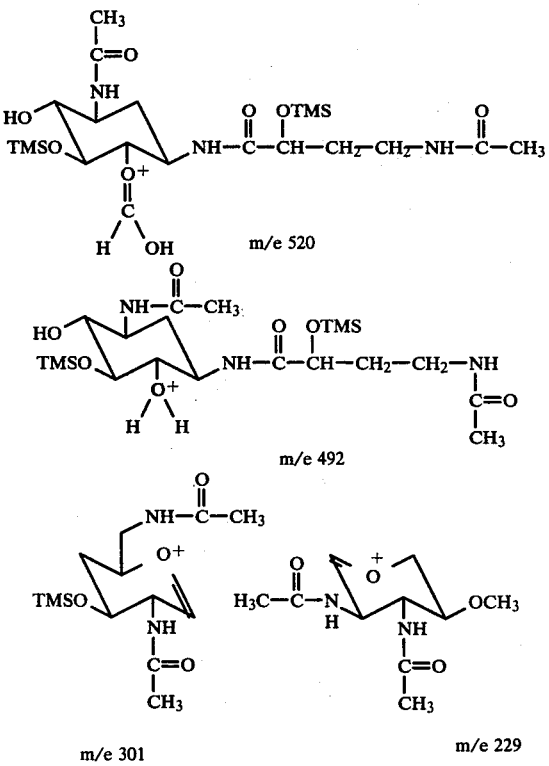

From the above physicochemical and biological properties, the powder is identified as the compound which comprises 1-N-[L-(—)-α-hydroxy-γ-aminobutyryl)-XK-88-5.

EXAMPLE 3

Preparation of sulfate of
1-N-[L-(—)-α-hydroxy-γ-aminobutyryl]-XK-88-5

In this example, 1.0 g of 1-N-[L-(—)-α-hydroxy-γ-aminobutyryl]-XK-88-5 obtained by the same manner as described in Example 2 is dissolved in 5 ml of water and the solution is adjusted to pH 4.5 with 6 N sulfuric acid. 250 ml of methanol is gradually added to the solution under cooling with stirring. The white precipitate formed is separated by filtration, washed with methanol and dried in vacuo to obtain 1.5 g of trisulfate of 1-N-[L-(—)-α-hydroxy-γ-aminobutyryl]-XK-88-5.

EXAMPLE 4

Preparation of L-α-hydroxy-γ-N-tertiary butyloxycarbonylaminobutyric acid

In this example, 1.19 g (10.0 mM) of L-α-hydroxy-γ-aminobutyric acid [Woo et al.: Tetrahedron Letters, P. 2617 (1971)] is dissolved in a mixed solvent of 20 ml of water-dioxane (1:1 by volume). The solution is adjusted to pH 10.0 with 2 N-sodium hydroxide, and 1.88 g (13.0 mM) of tertiary butyloxycarbonyl azido is added thereto. Then, the mixture is stirred at 25° C. for 7.5 hours. The reaction solution is maintained pH 9.5±0.5 with 2 N-sodium hydroxide all through the reaction.

To the resulting reaction mixture is further added 0.40 g of tertiary butyloxycarbonyl azide and the mixture is stirred at 25° C. for 6.5 hours. During the reaction the solution is also maintained pH 9.5±0.5. The resulting reaction mixture is extracted with 50 ml of ether. The water layer is adjusted to pH 4.6 with hydrochloric acid and concentrated to about 8 ml under reduced pressure at below 35° C., and 20 ml of ethyl acetate is added thereto. The solution is adjusted to pH 1.2 with hydrochloric acid under ice-cooling with vigorous stirring. The ethyl acetate layer is removed immediately. The water layer is quickly extracted three times each 20 ml of ethyl acetate. The ethyl acetate extracts are combined and washed with 5 ml of water and then dried over anhydrous sodium sulfate. Then, the ethyl acetate is removed under reduced pressure. As the result, L-α-hydroxy-γ-N-tertiary butyloxycarbonylaminobutyric acid is obtained as a glass.

(1) Specific rotation: $[\alpha]_D^{25} = -3.6°$ (c=1.00, CH$_3$OH)

(2) Elementary analysis as $C_9H_{17}O_5N$: Calculated (%); C=49.30, H=7.83, N=6.39 Found (%); C=48.79, H=7.85, N=6.55

(3) Nuclear magnetic resonance spectrum (in D$_2$O) τ 8.57 (9H, singlet), τ 7.93–8.27 (2H, multiplet), τ 6.60 (2H, triplet), τ 5.70 (1H, doublet-doublet)

EXAMPLE 5

Preparation of N-hydroxysuccinimide ester of
L-α-hydroxy-γ-N-tertiary
butyloxycarbonylaminobutyric acid In this example, 0.22 g (1.00 mM) of L-α-hydroxy-γ-N-tertiary butyloxycarbonylaminobutyric acid and 0.115 g (1.00 mM) of N-hydroxysuccinimide are dissolved in 16 ml of ethyl acetate. To the solution is added 0.21 g (1.02 mM) of N,N'-dicyclohexylcarbodiimide at —5° C. The mixture is allowed to stand at —18° C. for 2.5 hours, and further at 5° C. for 15 hours. To the resulting reaction mixture is added 0.05 ml of acetic acid and the mixture is allowed to stand at room temperature for one hour. The precipitate of N,N'-dicyclohexylurea is removed by filtration and the resulting filtrate is extracted two times each with 5 ml of water. The ethyl acetate layer is dried over anhydrous sodium sulfate and then ethyl acetate is removed under reduced pressure. The resulting residue is allowed to stand at room temperature one day and is solidified. As the result, 0.31 g of N-hydroxysuccinimide ester of L-α-hydroxy-γ-N-tertiary butyloxycarbonylaminobutyric acid is obtained. The analytical sample is recrystallized from benzene-n-hexane.

(1) Melting point: 104°–108° C.

(2) Specific rotation: $[\alpha]_D^{24} = +8.1°$ (c=1.00, CH$_3$OH)

(3) Elementary analysis as $C_{13}H_{20}O_7N_2$: Calculated (%); C=49.35, H=6.39, N=8.86 Found (%); C=49.37, H=6.35, N=8.93

(4) Infrared absorption spectrum (KBr, cm$^{-1}$) 1810, 1775, 1740, 1680

(5) Nuclear magnetic resonance spectrum (in CDCl$_3$) τ 8.57 (9H, singlet), τ 7.73–8.10 (2H, multiplet), τ 7.13 (4H, singlet), τ 6.57 (2H, quartet), τ 6.20 (broad), τ 5.31 (1H, triplet), τ 4.80 (1H, broad triplet)

EXAMPLE 6

Preparation of
1-N-(L-α-hydroxy-γ-aminobutyryl)-XK-88-5

In this example, 0.43 g (0.74 mM) of 6'-N-benzyloxycarbonyl-XK-88-5 [Compound (V)] is dissolved in 40 ml of water-tetrahydrofuran (1:1 by volume). To the solution is added 0.25 g (0.80 mM) of N-hydroxysuccinimide ester of L-α-hydroxy-γ-N-tertiary butyloxycarbonylaminobutyric acid dissolved in 8 ml of tetrahydrofuran and then the mixture is stirred at room temperature for 18 hours. The solvent is removed under reduced pressure at below 35° C. The resulting residue is dissolved in 10 ml of 90% trifluoroacetic acid and 5 ml of methanol. To the solution is added 0.30 g of 10% palladium carbon and then hydrogen gas is passed through the solution at room temperature for 7 hours. The palladium carbon is removed by filtration and methanol, tetrahydrofuran and water are removed under reduced pressure at below 35° C.

Isolation and purification of 1-N-(L-α-hydroxy-γ-aminobutyryl)-XK-88-5 from the resulting residue is carried out by the same manner as described in Example 2. As the result, 15 mg of 1-N-(L-α-hydroxy-γ-aminobutyryl)-XK-88-5 is obtained.

What is claimed is:

1. A composition of matter having an antibacterial activity represented by the formula:

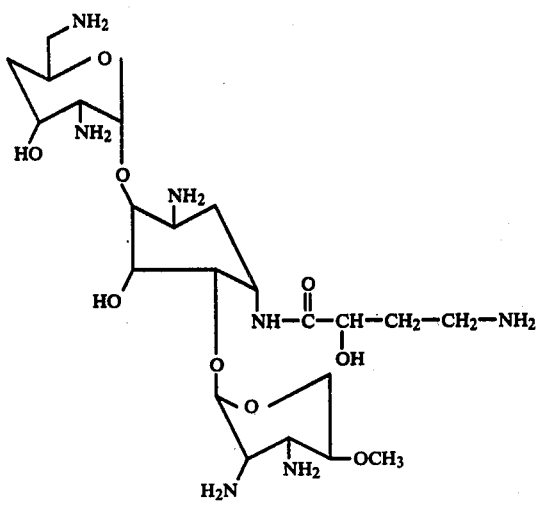

and the pharmaceutically acceptable non-toxic acid addition salts thereof.

2. A nontoxic pharmaceutically acceptable acid addition salt of the composition of matter of claim 1, wherein said acid is selected from the group consisting of hydrochloric acid, hydrobromic acid, hydriodic acid, sulfuric acid, phosphoric acid, carbonic acid, nitric acid, acetic acid, fumaric acid, malic acid, citric acid, mandelic acid, ascorbic acid, tartaric acid and succinic acid.

* * * * *